United States Patent [19]

Sarrine

[11] 4,360,016
[45] Nov. 23, 1982

[54] BLOOD COLLECTING DEVICE

[75] Inventor: Robert J. Sarrine, Ann Arbor, Mich.

[73] Assignee: Transidyne General Corp., Ann Arbor, Mich.

[21] Appl. No.: 165,155

[22] Filed: Jul. 1, 1980

[51] Int. Cl.³ .......................................... A61B 10/00
[52] U.S. Cl. ................................ 128/763; 128/769; 128/770; 128/329 R
[58] Field of Search ............... 128/329, 314, 315, 770, 128/769, 304, 763–766

[56] References Cited

U.S. PATENT DOCUMENTS

| | | | |
|---|---|---|---|
| 2,442,416 | 6/1948 | Kulicke, Jr. | 128/314 |
| 2,705,949 | 4/1955 | Silverman | 128/329 |
| 3,030,959 | 4/1962 | Grunert | 128/329 |
| 3,517,670 | 6/1970 | Speelman | 128/314 |
| 3,685,509 | 7/1970 | Bentall | 128/2 F |
| 3,741,197 | 6/1973 | Sanz et al. | 128/2 F |
| 3,760,809 | 9/1973 | Campbell, Jr. | 128/314 |
| 3,811,326 | 5/1974 | Sokol | 73/425.4 P |
| 4,170,232 | 10/1979 | Khoury | 128/351 |

Primary Examiner—Kyle L. Howell
Assistant Examiner—Nancy A. B. Swisher
Attorney, Agent, or Firm—Krass, Young & Schivley

[57] ABSTRACT

A blood collecting device (10) includes a lancet (40) and a capillary tube (30) carried together by an elongated member (14). The tube (30) is simultaneously positioned adjacent the skin when the lancet (40) is advanced by the member (14) to puncture the skin. The lancet (40) is automatically retracted by a retraction spring (54) but the tube (30) is maintained in close proximity with the puncture for collecting blood issuing therefrom without further manipulation by the user.

17 Claims, 7 Drawing Figures

BLOOD COLLECTING DEVICE

TECHNICAL FIELD

This invention relates generally to blood collecting apparatus and, more particularly, to fetal blood sampling devices.

BACKGROUND ART

Fetal blood sampling is extensively employed during births where the doctor suspects that the infant may be receiving an improper supply of oxygen due, for example, to strangulation by the umbilical cord or premature separation of the placenta. Conventionally, such sampling involves passing an endoscope through the birth canal and pressing it onto the fetal presentation. The field is swabbed as dry as possible with long swab holders projecting through the endoscope, and a jelly is similarly applied to induce a large drop of blood to form. The doctor then introduces a lance through the endoscope to make an incision. After the incision is made, the lance is removed and a long glass capillary tube is advanced to collect a sample of the blood.

This technique is associated with difficulty since fetal movement often occurs to change the field and contamination of the drop of blood is possible which results in errors in pH readings. In practice, the movement of the fetal part and the fact that the procedure is carried out at a distant vision causes some difficulty in easily obtaining a sample and, even then, the results so obtained may not be completely reliable. Moreover, this technique is relatively time consuming and clumsy in that a plurality of different parts must be inserted and removed in a series of separate steps.

One attempt to avoid the problems noted above is disclosed in U.S. Pat. No. 3,685,509 to Bentall which discloses a fetal blood sampling endoscope having an evacuated tubular end portion for adhering to the body part. A non-removable custom-formed capillary tube is threaded through the walls of the device until one end of the tube is flush with the part engaging the end of the endoscope. A lance freely movable in the endoscope is manually advanced to puncture the skin, with the capillary tube disclosed as being capable of collecting blood issuing therefrom. The disclosed technique has several drawbacks. This concept introduces a new requirement for additional equipment in that suction must be applied to annulus of the endoscope. The necessity for additional equipment is both costly and burdensome. The hand-held lance which is freely moveable in the device must be manually aimed by the doctor and guided onto a target point on the body in order to make a properly located incision which may be collected by the capillary tube. The doctor may encounter some difficulty in accomplishing this feat. It has been discovered that skin adjacent the puncture may cover the end of the capillary tube when the tube is flush with a squared off end surface such as shown in this reference. Finally, the capillary tube of the reference is not removable thereby requiring a relatively large quantity of blood to be collected or necessitating the use of external suction to obtain the blood from the opposite tube end.

The present invention is directed to solving one or more of the problems set forth above.

DISCLOSURE OF THE INVENTION

In one aspect of the invention a blood collecting device is provided with an elongated member having a lancet tip for puncturing skin. A capillary tube is mounted on the member and is simultaneously positioned adjacent the skin when the tip is advanced by the member to puncture the skin. Provision is made for retracting the lancet while maintaining the tube in close proximity with the puncture whereby blood issuing thereby is collected by the tube. Preferably, the elongated member includes a collar at one end thereof which slopes at an angle and the capillary tube is spaced from the outer surface of the collar. The collar is discontinuous to prevent miniscus action during the blood collecting process. In one embodiment the device takes the form of a ballpoint pen like structure in which retracting springs are mounted in a portion of the member. The capillary tube is removably mounted on the member so that it may be separately carried away for further processing of the blood. Means are provided for automatically spacing the collecting end of the tube a desired distance from the outer surface of the collar.

BRIEF DESCRIPTION OF THE DRAWINGS

These and other objects and advantages of the present invention will become apparent upon reading the following specification and by reference to the drawings in which:

FIGS. 4-7 illustrate a method of using the device of the present invention.

BEST MODE FOR CARRY OUT THE INVENTION

Figure 1:
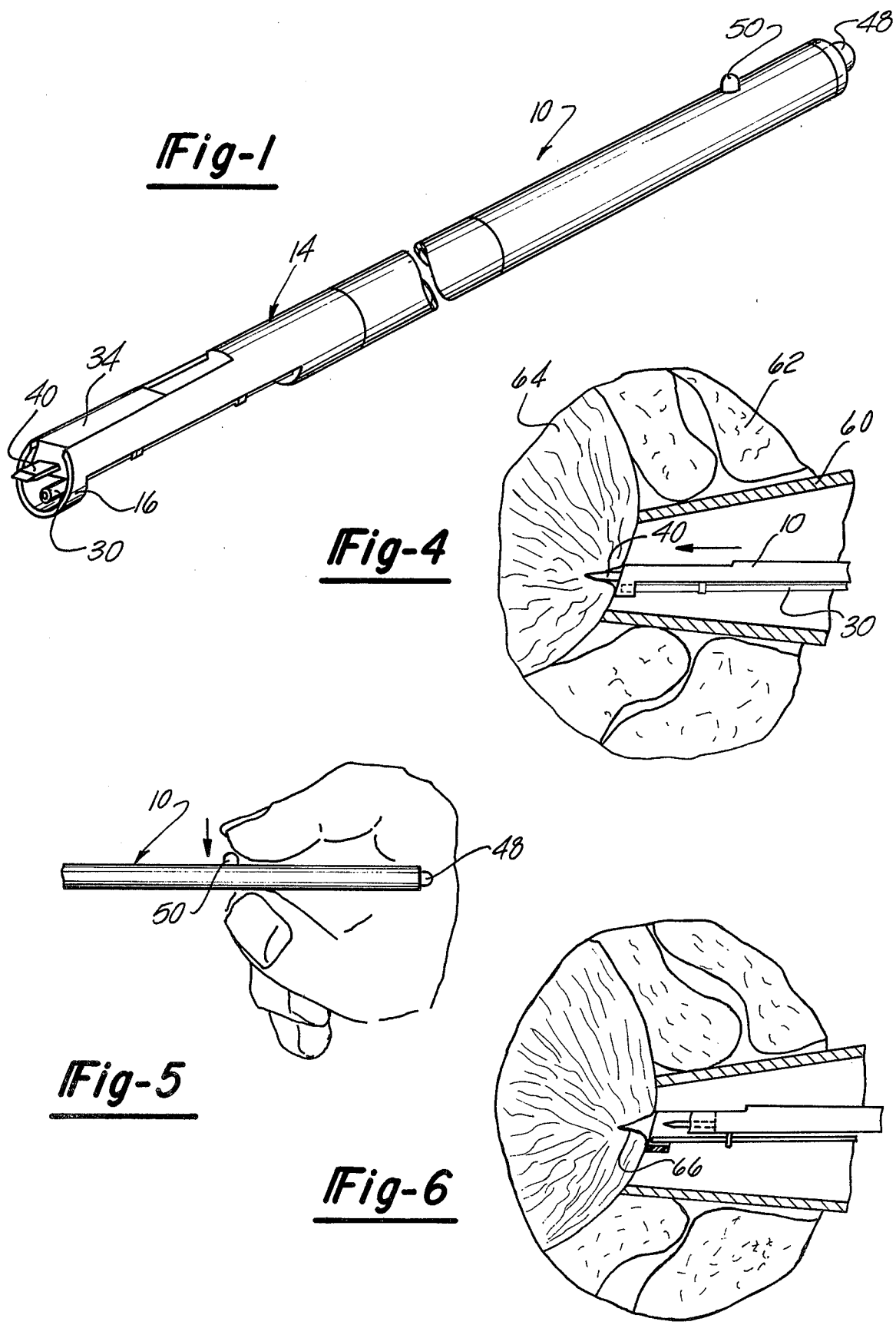
FIG. 1 is a perspective view of the preferred embodiment of this invention.
Figure 2:
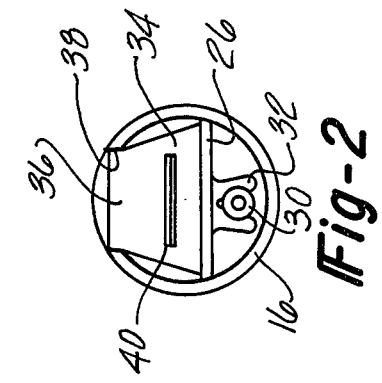
FIG. 2 is an end view thereof.
Figure 3:
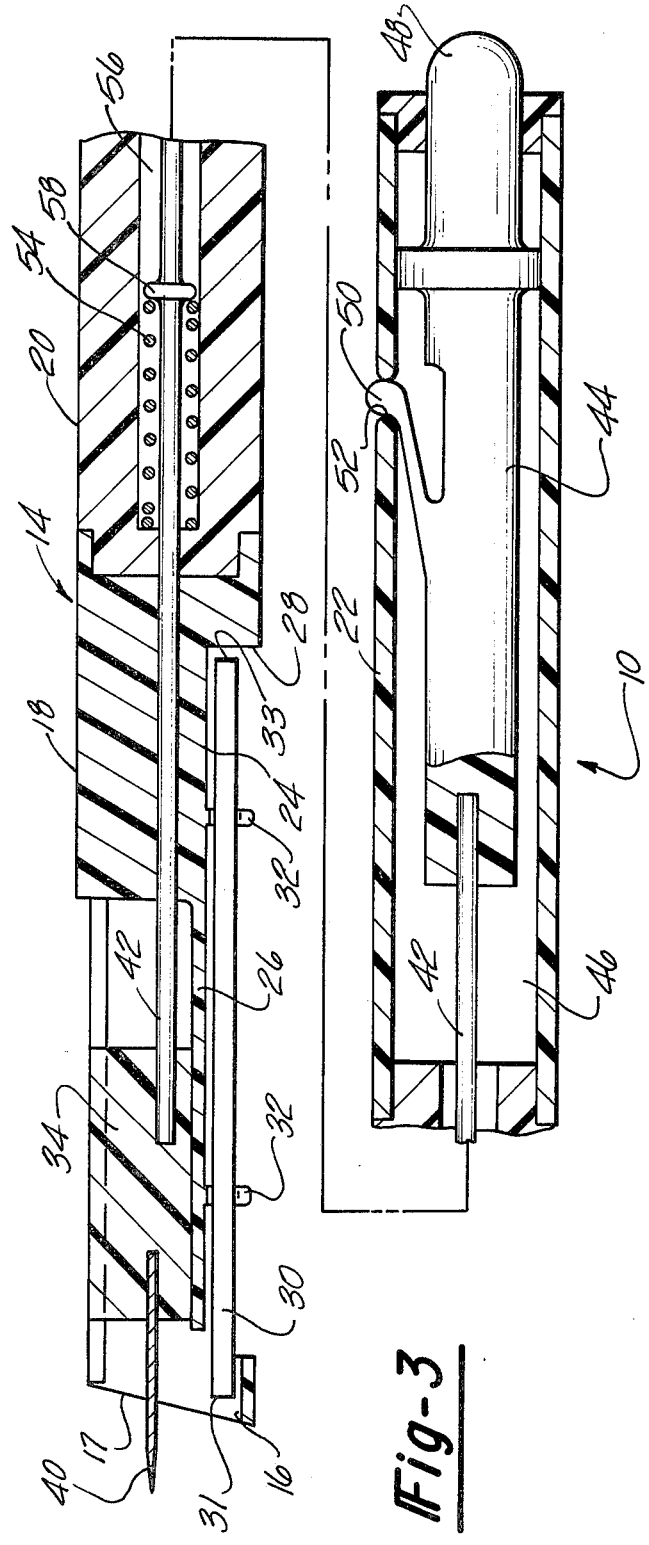
FIG. 3 is a cross sectional view thereof.

The blood collecting device 10 of the present invention finds particular utility in collecting a fetal blood sample although it has applicability for collecting fluid issuing from tissues in a variety of applications. Device 10 includes an elongated tubular member generally designated by the numeral 14 which resembles a ballpoint pen. With reference to FIGS. 1-3, the distal end of member 14 includes a collar 16. The outer surface 17 of collar 16 slopes at an angle with respect to the transverse axis of member 14. The angle is chosen to compliment the angle of the presenting part through the cervix. Preferably, the angle is between 10-20 degrees and more particularly, about 16 degrees. Collar 16 has an outside diameter of about 0.25 inch with a wall thickness of about 0.025 inch in this nonlimiting example.

Member 14 in the particular embodiment shown includes three generally concentric sections 18, 20, and 22 which are screwed together. Section 18 includes a cut away portion 24 about its lower surface. Cutaway portion 24 is defined by a flat surface 26 extending parallel to the major longitudinal axis of member 14 and generally bisecting section 18 as is most clearly shown in FIG. 2. A transversely extending wall 28 provides a stop for one end of a capillary tube 30. Resilient clips 32 extending downwardly from surface 26 operate to hold tube 30 in a fixed position. Abuttment of the tube end 33 against wall 28 will automatically position the blood collecting end 31 of tube 30 within the confines of collar 16 and a predetermined distance from the outer surface 17 thereof. Preferably, the blood collecting end 31 is spaced about 0.005-0.025 inch from the outer collar surface 17.

A wedge 34 is slidably mounted on surface 26. As shown most clearly in FIGS. 1 and 2, wedge 34 is substantially triangular in cross section and includes an upwardly extending ridge 36. A slot in section 18 runs through collar 16 inwardly for a substantial distance. Slot 38 serves several functions. First, it breaks the continuity of collar 16 to prevent miniscus action which could degrade the blood collection process in capillary tube 30. Further, slot 38 cooperates with ridge 36 to provide a longitudinally directed guide way for wedge 34 while at the same time preventing lateral movement thereof. In this embodiment, the slot 38 is approximately 0.12 inch wide. The upper walls of section 18 also cooperate with surface 26 to provide a track for wedge 34.

A lancet blade 40 adapted to puncture skin is connected to one end of wedge 34. The opposite end of wedge 34 is connected to a rod 42. The opposite end of rod 42 passes through the remaining portion of section 18, through section 20 and into section 22 where it is connected to a plunger 44. Plunger 44 is mounted for reciprocating movement within the cavity 46 of section 22. Plunger 44 includes a head 48 extending from the proximal end of section 22. A resilient finger 50 on plunger 44 is adapted to engage an opening 52 in the walls of section 22 when plunger 44 has been removed to the position shown in FIG. 3.

The intermediate section 20 includes a retraction spring 54 within the hollowed out portion 56. A transversely extending plate 58 operates to compress spring 54 when the plunger 44 is pressed. When finger 50 engages opening 52, wedge 34 is positioned so that blade 40 projects within 0.12 inch and preferably about 0.080 inch from the outer surface 17 of collar 16. When the finger 50 is pressed inwardly to disengage it from opening 52, retraction spring 54 operates to urge wedge 34 rightwardly to move blade 40 inwardly along surface 26 to bring blade 40 inboard of collar surface 17.

INDUSTRIAL APPLICABILITY

The present invention will now be described in connection with taking a fetal blood sample. Referring to FIG. 4, a conventional endoscope 60 is advanced in the cervix 62 until its end rests upon the presenting part such as the infant's head 64. The doctor presses head 48 of plunger 44 until finger 50 is engaged with opening 52. This will cause the blade 40 to project a predetermined distance from collar surface 17. The device 10 is inserted through endoscope 60 until collar surface 17 rests flush against the skin of head 64 with blade 40 puncturing the skin. Thus, it can be appreciated that collar 16 provides a stop for controlling the depth of the incision or puncture 66 made by the blade 40.

Figure 7:
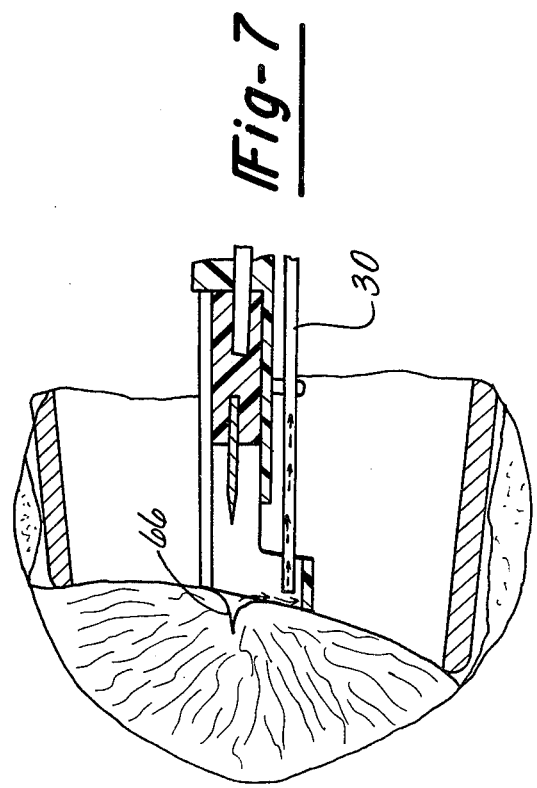

Turning now to FIGS. 5 and 6, after making the incision the doctor then presses finger 50 to cause the blade 40 to retract within the outer surface 17 of collar 16. Note, however, that the collecting end 31 of capillary tube 30 is maintained in a close proximity with the puncture 66 without requiring any further movement of the device 10. When the blade is retracted as shown in FIG. 7, the blood issuing from the puncture 66 falls by gravity into the lower confines of collar 16 where it is collected by capillary action into the bore of tube 30. By spacing the tube collecting end 31 from the collar outer surface 17, the possibility of the infant's skin covering end 31 is reduced. The angled end of collar 16 further aids against this condition which would degrade the ability of tube 30 to collect blood. The surface of the skin of the infant lies at a generally obtuse angle as viewed through the cervix. The angle of collar 16 is chosen to be substantially complimentary with the infant's angle such that the collar surface 17 will be flush with the skin surface. The protruding lower part of collar 16 act as a dish for collecting the blood and directing it towards the collecting tube end 31. Note also that the tube 30 lies generally parallel with the elongated member 14 and thus at an angle with respect to the collar surface 17. Therefore, the skin, even if it projects a sufficient amount into collar 16 to touch the tube end 31, it will be at an angle such that the tube end 31 is not completely blocked off.

After the blood has been collected into tube 30, the doctor merely retracts the entire device 10. The conventional straight capillary tube 30 is then removed from its retaining clip 32 for processing the blood.

It can now be appreciated from the foregoing description that the broad concept of this invention involves a device in which both the lancet and the blood collecting capillary tube are part of a unitary device for moving in unison until the puncture is made. Thus, the somewhat clumsy and unreliable approach of the prior art is greatly simplified. The lancet and the capillary tube are carried together in a predefined position until the puncture is made, with the blade being subsequently automatically retracted while maintaining the tube in close proximity with the puncture so that blood issuing from the puncture is readily collected from the tube without further manipulation from the doctor. It is envisioned that device 10 lends itself to being formed by injection plastic molding or the like and that various means for retracting the lancet will become apparent to one skilled in the art. Other modifications will become apparent upon study of the specification, drawings, and claims.

I claim:

1. A fluid collecting device (10) comprising an elongated member (14), puncturing means (40) carried by said member for puncturing tissue, and means (32) also carried by said member (14) for connecting a capillary tube (30) to the member such that an end (31) of the capillary tube is maintained in a predetermined space relationship with said puncturing means whereby the tube end is automatically positioned adjacent to the punctured tissue for collecting blood issuing therefrom.

2. The device of claim 1 which further comprises:
means (54) for retracting the puncturing means (40) while maintaining a relationship of close proximity between the tube (30) and the puncture.

3. The device of claim 1 wherein said member (14) includes an end portion (16) for engaging the tissue.

4. The device of claim 3 wherein said end portion (16) slopes at an angle with respect to the transverse axis of the member (14).

5. The device of claim 3 wherein said member end comprises a generally annular collar (16), with said tube collecting end (31) being within the confines of said collar (16) for collecting said fluid.

6. The device of claim 5 wherein said collar is discontinuous (38) to prevent miniscus action during the blood collection process.

7. The device of claim 3 wherein said puncturing means (40) initially projects a distance from said one end (16), with said end (16) providing a stop for controlling the depth of said puncture.

8. The device of claim 7 wherein said tube (30) generally parallels the longitudinal axis of said member (14), said tube (30) having a collecting end (31) which is spaced from the outer surface (17) of said member end (16) and located beneath said puncturing means (40).

9. The device of claim 8 wherein said member (14) includes means for automatically spacing the collecting end (31) a predetermined distance from the outer surface (17) of said member end (16).

10. The device of claim 9 wherein said automatic spacing means comprises an abutment surface (28) for the opposite end (33) of the tube (30).

11. A fetal blood collecting device (10) comprising:
an elongated pen-like member (14) having a collar (16) on a distal end thereof having its outer surface (17) sloped with respect to the transverse axis of the member (14), and being adapted to engage the presenting part of the fetus disposed at a complimentary angle in the cervix, said member (14) having a cut away portion (24) with a substantially flat surface (26) extending inwardly from said collar (16) generally parallel with the longitudinal axis of said member (14), said cut away portion (24) having a transversely extending wall (28) spaced a predetermined distance from said collar (16), wedge means (34) slidably mounted for laterally restricted longitudinal movement on said flat surface (26) of the cut away portion (24), a blade (40) connected to one end of said wedge (34) with, a rod (42) connected to the opposite end of said wedge (34) and slidably mounted in said member (14), operative to move the wedge (34) to a first position with the blade (40) projecting a given distance from said collar (16) and within the confines thereof, means (32) carried by said flat surface (26) for removably holding a capillary tube (30) generally parallel with said longitudinal axis of the member (14) so that an end (31) of the tube is within the confines of said collar at a predetermined spaced relationship below the blade protruding from the collar whereby the tube is automatically positioned adjacent the tissue punctured by the blade for collecting blood issuing therefrom, said wall (28) serving to automatically space the tube end (31) a predetermined distance from the outer surface (17) of said collar (16); and retraction means (54) connected to said rod (42) for retracting the blade (40) inwardly of said collar (16) after puncturing the tissue while maintaining the tube end (31) adjacent the tissue.

12. The device of claim 11 wherein said collar surface (17) is sloped at an angle of 10-20 degrees.

13. The device of claim 11 wherein said capillary tube (30) is spaced between 0.005-0.025 inch from the outer surface (17) of said collar (16).

14. The device of claim 11 which further comprises a slot (38) extending along upper portions of said member (14) through the collar (16) and above the cut away portion (24); said wedge (34) having a ridge portion (36) projecting into said slot (38).

15. A blood collection device comprising:
an elongated member (14) terminating in a generally annular collar (16) at one end for engaging tissue;
puncturing means (40) mounted on said member and operative to protrude a given distance from the collar (16) to puncture tissue; and
means (32) also carried by said member (14) for securing an end (31) of a capillary tube (30) within the confines of said collar (16) and below said puncturing means (40) in a predetermined spaced relationship therewith whereby said tube end is automatically maintained in a position to collect blood issuing from a puncture made by the puncturing means (40) without further substantial movement of said member (14).

16. The device of claim 15 which further comprises means (54) for retracting said puncturing means (40) while maintaining a relationship of close proximity between the tube (30) and the puncture.

17. A method of collecting fluid from tissues, said method comprising:
connecting a capillary tube to a device having a puncturing portion at one end thereof so that an end of the tube is maintained in a predetermined spaced relationship below the puncturing portion;
advancing the device in one continuous movement to substantially simultaneously puncture the tissue with the puncturing portion and position the end of the tube in close proximity with the puncture; and
collecting fluid emanating from the puncture into the end of the capillary tube without further movement of the device with respect to the tissue.

* * * * *